(12) United States Patent
Li et al.

(10) Patent No.: US 12,185,674 B2
(45) Date of Patent: Jan. 7, 2025

(54) METHOD FOR INHIBITING MICROBIAL CLOGGING IN DRIP IRRIGATORS

(71) Applicant: CHINA AGRICULTURE UNIVERSITY, Beijing (CN)

(72) Inventors: Yunkai Li, Beijing (CN); Peng Song, Beijing (CN); Hongxu Zhou, Beijing (CN)

(73) Assignee: CHINA AGRICULTURE UNIVERSITY (CN)

( * ) Notice: Subject to any disclaimer, the term of this patent is extended or adjusted under 35 U.S.C. 154(b) by 456 days.

(21) Appl. No.: 17/598,747

(22) PCT Filed: Mar. 29, 2019

(86) PCT No.: PCT/CN2019/080390
§ 371 (c)(1),
(2) Date: Sep. 27, 2021

(87) PCT Pub. No.: WO2020/198926
PCT Pub. Date: Oct. 8, 2020

(65) Prior Publication Data
US 2022/0322620 A1    Oct. 13, 2022

(51) Int. Cl.
*A01G 25/02* (2006.01)
*C12N 1/20* (2006.01)
*C12Q 1/10* (2006.01)

(52) U.S. Cl.
CPC .............. *A01G 25/02* (2013.01); *C12N 1/205* (2021.05); *C12Q 1/10* (2013.01)

(58) Field of Classification Search
CPC ........ A01G 25/02; A01G 25/06; C12N 1/205; C12N 1/20; C12Q 1/10; C12Q 1/02; C12Q 1/689; A01N 63/22; A01P 1/00; Y02A 40/22; Y02E 50/30
See application file for complete search history.

(56) References Cited

FOREIGN PATENT DOCUMENTS

| CN | 103752560 | A | * | 4/2014 | ............... | B08B 3/08 |
|----|-----------|---|---|--------|----------------|-----------|
| CN | 107151189 | A | * | 9/2017 | ............... | C05D 9/02 |

OTHER PUBLICATIONS

Sahin et al., "Biological treatment of clogged emitters in a drip irrigation system", Journal of Environmental Management 76 (2005), pp. 338-341 (Year: 2005).*
Sattley, W. Matthew, and Michael T. Madigan. "Microbiology." eLS (2015), pp. (Year: 2015).*
Zhou Bo et al., "Formulation of an Emitter Clogging Control Strategy for Drip Irrigation With Reclaimed Water", Irrig. and Drain. (2016), pp. 1-10 (Year: 2016).*
Zhou et al., "Effects of microbial community variation on bio-clogging in drip irrigation emitters using reclaimed water", Agricultural Water Management 194 (2017), pp. 139-149 (Year: 2017).*
Translation of Huang et al., CN107151189A , from Espacenet Patent Translate (Year: 2017).*
Deng, Y., et al. "Molecular ecological network analyses". BMC Bioinformatics 13, 113 (2012), pp. doi.org/10.1186/1471-2105-13-113, pp. 1-20 (Year: 2012).*
Translation of Li et al, CN103752560A from Espacenet Patent Translate (Year: 2014).*

* cited by examiner

*Primary Examiner* — Terry A McKelvey
*Assistant Examiner* — Andrew T Moehlman
(74) *Attorney, Agent, or Firm* — Emerson, Thomson & Bennett, LLC; Roger D. Emerson; Matt J. Wilson

(57) ABSTRACT

A method for inhibiting microbial clogging of drip irrigation emitters, belonging to the technical field of water-saving irrigation. The method includes the following steps: (1) Use developmental molecular ecological network analysis to determine the key bacteria causing the clogging of drip irrigation emitters, and then carry out screening of antagonistic bacteria to inhibit the clogging of drip irrigation emitters; (2) Ferment the selected antagonistic bacteria in a medium containing biogas slurry, to generate bacterial antagonist; (3) Apply the bacterial antagonist to drip irrigation system. The method uses the molecular ecological network analysis method to obtain key bacteria that cause the growth of biofilm in drip irrigation emitters, and then combines the principle of microbial antagonism to screen out the antagonistic bacteria that can antagonize the growth of biofilm, so as to inhibit the growth of biofilm in irrigation emitters.

7 Claims, 3 Drawing Sheets
Specification includes a Sequence Listing.

METHOD FOR INHIBITING MICROBIAL CLOGGING IN DRIP IRRIGATORS

TECHNICAL FIELD

This invention belongs to the technical field of water-saving irrigation, which specifically relates to a method for inhibiting microbial clogging of drip irrigation emitters.

BACKGROUND

Drip irrigation technology is currently considered to be the most effective water-saving irrigation method. It can accurately transport water and fertilizer to the roots of plants, which is the development direction of water-saving irrigation. With the intensification of water scarcity and pollution problem, the use of unconventional water resources such as reclaimed water, surface water of rivers, lakes and reservoirs, rainwater and aquaculture wastewater in a drip irrigation system has exacerbated the problem of clogging in key components of the drip irrigation system The clogging of an irrigation emitter caused by unconventional water resources is mainly due to a biological clog. The growth of a biofilm clog causes corrosion and damage to filter equipment, increasing hydrodynamic resistance and thus increasing energy consumption, and also increasing the clogging of water pipelines and irrigation channels, so as to make the water delivery efficiency and irrigation application uniformity seriously reduced. And even more, it may lead to the scrapping of the entire system. Therefore, the solution of the clogging problem directly determines the service life and application benefit of a drip irrigation project.

How to effectively remove and control the growth of biofilm is the key for solving the clogging problem of drip irrigation emitter. A large number of scientific research scholars have conducted a lot of research on this, including: chemical chlorination, regular backwashing, pulsed flow cleaning technology, microbubble technology, surface modification, surface coating technology, ultraviolet light, intense magnetic field, ultrasound, colony quenching technology, etc. But in general, the existing methods have certain defects in terms of application cost, environmental pollution, resource consumption and operating energy consumption. Microbial colony propagation and growth are the key reasons why it is difficult to remove the epiphytic biofilm inside the pipeline. Taking advantage of antagonistic relationship of microorganisms, it can inhibit or even kill the key microorganisms that generate biofilms, so as to interfere with and control the formation and development of biofilms. This provides a new green and environmental control idea for limiting the growth of epiphytic biofilm.

For example, Gao Shengguo et al. (CN202168387U) of the Institute of Farm Irrigation, Chinese Academy of Agricultural Sciences, disclosed an anti-biological clogging device for drip irrigation system, which making use of the ozone generator to effectively kill microorganisms in flow channels. However, after ozone has dissolved in water, it has a negative impact on the soil microbial community and reduces the soil health quality. Bai Zhihui et al. (CN106957804A) disclosed a microbial control method for preventing and controlling the clogging of drip irrigation emitters. This method proposed to use the selected *Bacillus subtilis* Nl4 strain to alleviate the clogging of drip irrigation emitters. And it can restore the flow rate of the clogged emitters. However, in view of the complexity of irrigation water quality, it is debatable whether this strain has beneficial microbial control effects for different water sources. Therefore, with the introduction of molecular ecological network analysis (MENA), a feasible method has been proposed to determine the key bacteria that affect the growth of biofilms, but there is no related patent and literature to report.

DESCRIPTION OF THE INVENTION

In order to overcome the problems in the existing technologies, this invention puts forward a method for the clogging of drip irrigation systems using different irrigation water sources, which can effectively solve the clogging of drip irrigation emitters caused by irrigation water sources. For this, the technical scheme of the invention is as follows: a method for inhibiting the clogging of drip irrigation emitter, including the following steps:

(1) Use developmental molecular ecological network analysis to determine the key bacteria causing the clogging of drip irrigation emitter, and then carry out screening of antagonistic bacteria to inhibit the clogging of drip irrigation emitter;

(2) Ferment the selected antagonistic bacteria in a medium containing biogas slurry, to generate a bacterial antagonist.

(3) Apply the bacterial antagonist to drip irrigation system

In the above method, the screening of antagonistic bacteria includes the following steps:

(1) Cultivate the epiphytic biofilm in the channel of irrigation emitter, and then extract microorganisms in the clogging biofilm; (2) Extract the total DNA of the microorganisms in the biofilm, expand the V3-V4 variable region of 16S rRNA, purify, quantitatively detect and sequence; (3) Apply the sequencing result of biofilm microorganisms to construct a phylogenetic molecular ecological network, and then screen out the key bacteria that affect the growth of biofilm based on the correlation among bacteria. At the same time, according to the crops to be irrigated, select the bacteria with biological control function, wherein one of ordinary skill in the art would understand that the control function means the selected bacteria will not affect the growth of the crops to be irrigated, as candidate bacteria, and then combine the key bacteria selected above to conduct an antagonism experiment to determine if the bacteria with biological control function antagonizes growth of the microorganisms in the clogging biofilm. The strains in candidate bacteria which have antagonistic effect against the key bacteria are used as antagonistic bacteria.

In the above method, the cultivating of an epiphytic biofilm in the flow channel of irrigation emitter can adopt the following methods, including: using the comprehensive test device (CN102288409A) of anti-clogging performance for drip irrigation emitter to carry out biofilm cultivation. Biofilm extraction is performed when the clogging degree of the irrigation emitter reaches 50% or more.

In the above method, the construction and analysis method of phylogenetic molecular ecological network is as follows: first, carry out standardizing treatment on the raw data of OTU (operational taxonomic unit) of each strain, then use the MENA network analysis system to calculate the connection strength between OTU nodes; obtain the network property parameters through network analysis, and then carry out visual processing to obtain the network structure diagram; and find out the OTU with high number of links with other OTU, that is, the key bacteria affecting the growth of biofilm.

The construction and analysis of a phylogenetic molecular ecological network system can adopt the following methods.

First, obtain the original data of OTU abundance matrix according to the sequencing result, each row corresponding to an OTU and each column corresponding to an abundance of the OTU in different samples, so to carry out standardizing treatment on the raw data;

Use the MENA analysis website and the molecular ecology interface method based on the random matrix theory to construct a phylogenetic molecular ecological network system:

For example, the methods that can be used include: calculating the Pearson correlation of any two OTU and then constructing a correlation matrix; converting the correlation matrix into a similarity matrix; automatically set a similarity threshold according to the principle of random matrix, and then converting the similarity matrix into an adjacency matrix, so as to calculate the connection strength between OTU. Based on the default threshold, use the MENA network analysis (analyze the networks) to calculate the network property parameters.

Use Cytoscape 3.4.0 software to visualize the network; get the network structure diagram and related information: the number of nodes, that is, the strains in the community (OTU); the connection between nodes, that is, the interaction relationship between species (positive correlation, co-occurrence; negative correlation, competition); connectivity, the connection strength between a node and its other connecting nodes; geodesic distance, the shortest distance between two nodes; clustering coefficient, the connectedness between a node and other nodes; modularity, the module feature in a molecular ecological network. A network is divided into multiple modules. And a single module is considered as a functional unit in the ecosystem.

Finally, use the Maslov-Sneppen method, without changing the number of original network nodes and connections, to reconnect nodes at different locations in the original network and construct 100 random networks, and then compare the molecular ecological network and the random networks to find their differences.

Identification of key bacteria: the molecular ecological network of the biofilm bacterial community can reflect the interaction between the colonies. Among them, those whose OTU have a large number of links with other OTU are the key bacteria that affect the growth of biofilm. Controlling the key bacteria can inhibit the growth of biofilm, so as to remove the biofilm in drip irrigation emitter.

In the above method, the bacterial species with biological control function include: pathogenic bacteria that may cause crop disease during the growth period of drip irrigation crops and probiotic bacteria in the roots of crops that promote crop growth.

In the above method, the pathogenic bacteria include bacteria, viruses, fungi, or other pathogenic bacteria; the probiotic bacteria include *Agrobacterium, Azotobacter, Azospirillum, Bacillus, Burkholderia, Pseudomonas, Micrococcus, Rhizobium*, or *Frankia*.

In the above method, the preparation method of bacterial antagonist includes the following steps: concentrating the fresh biogas slurry, and then fermenting and cultivating the biogas slurry and the antagonistic bacteria to generate bacterial antagonist.

In the above method, the method of concentrating includes: putting the fresh biogas slurry into a reactor in vacuum state for concentration; the concentrating pressure is $1 \times 10^5$ Pa. The slurry is concentrated to moisture content as about 60%; and the concentrating time is about 1 h.

In the above method, the method of fermenting and cultivating the biogas slurry and the antagonistic bacteria includes: in parts by weight, adding 15-20 parts of antagonistic bacteria, 0.4-0.8 parts of sodium selenite and 6-8 parts of brown sugar into 75-85 parts of biogas slurry. Uniformly stirring and fermenting this mixed biogas slurry for 4-10 days at a temperature of 25-28° C. to obtain liquid bacterial fertilizer, and then applying micro-nano bubbles to the liquid bacterial fertilizer to obtain bacterial antagonist.

In the above method, the method of applying bacterial antagonist to the drip irrigation system includes: when the relative average flow of the irrigation emitter drops by 25% or after the system has been running for 100 hours, the produced antagonist is mixed in the drip irrigation source water in a mass ratio of 1:500-1500, and then input into the drip irrigation system.

In the above method, the method of applying bacterial antagonist to the drip irrigation system also includes: periodic application. The application frequency is 1 time/1 to 2 weeks, and 2 to 3 hours of each application.

The beneficial effects of this invention:

(1) The method of this invention uses molecular ecological network analysis to obtain the key bacteria that lead to the growth of biofilm in drip irrigation emitters. Combining the principle of microbial antagonism, the key bacteria that can antagonize the key bacteria leading to the growth of biofilm are screened out; and at the same time, according to the needs of drip irrigation crops, further selecting the probiotic bacteria that have biological prevention on crop diseases and rhizosphere growth promoting effects, so as to obtain multi-functional antagonistic bacteria with clogging control, biological control and growth promotion, which can be used in drip irrigation system to inhibit the growth of biofilm in irrigation emitters. The method is suitable for different irrigation water qualities. And it can solve the problem of irrigation emitter blockage in a pertinent and targeted manner.

(2) The method of this invention uses biogas slurry as a liquid fermentation medium to further screen out the dominant antagonistic bacteria that dominate the micro-nano bubble water drip irrigation process; and it uses the dominant antagonistic bacteria strains to produce bacterial antagonist, so as to realize the low-cost production of microbial agent for agricultural use.

(3) The method of this invention applies bacterial antagonist to drip irrigation system, combining with the application mode of multifunctional liquid bacterial antagonist to control the biological clogging of drip irrigation emitters. It can ensure the safe operation of the drip irrigation system for more than 300 hours, to realize the safe operation of the drip irrigation system and also the efficient utilization of unconventional water sources.

DETAILED DESCRIPTION

This invention will be further described below in conjunction with specific examples, but the scope of protection claimed by this invention is not limited to the scope of the examples. Anyone of ordinary skill in the art can produce other products in various forms under the enlightenment of this invention. However, no matter what changes in the shapes or component ratios of such other products, once their technical solutions are the same or similar to those of this invention, they shall fall within the protection scope of this invention. The materials and devices used in this invention are all commercially available unless otherwise specified.

Example 1

Figure 1:
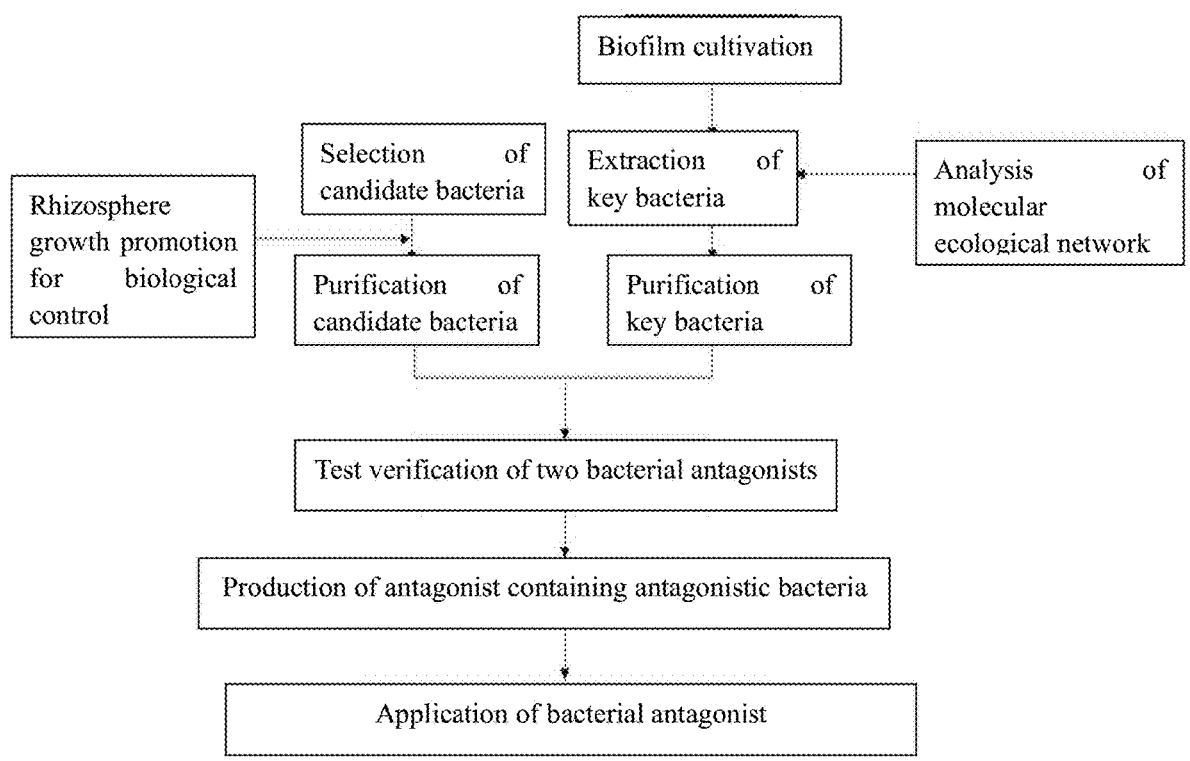
FIG. 1 is a flowchart of the method for inhibiting microbial clogging of drip irrigation emitter.

The invention can be widely applied to control the clogging of drip irrigation system using unconventional water sources. We take the blockage removal of reclaimed water drip irrigation emitter as an example to introduce the implementation process of this invention. And the process is as shown in FIG. 1.

It includes the following steps:
(1) Cultivation of Clogging Biofilm

Two kinds of reclaimed water sources are processed by cyclic activated sludge system (CASS) and sequencing batch aeration wastewater recycling technology (SBWL) to meet the standards and used as test water sources. Their water quality test results are shown in Table 1.

A comprehensive test device for anti-clogging performance for drip irrigation emitter (see CN102288409A for details) is used for biofilm cultivation. In the experiment, 6 irrigation emitters with different flow channel structures are used for biofilm cultivation. The structure parameters of the irrigation emitters are shown in Table 2.

Before the experiment, use NaClO solution to sterilize the entire device, storage bucket, etc., and then rinse with deionized water. A 120-mesh laminated filter is set up as a filtration treatment system. During operation, the operating pressure of the system is maintained at 100 kPa; and the system runs for 14 hours (7:00-21:00) every day; the system has run for 784 hours for a total of 56 days. The filter is cleaned every 3 days; and the water in the storage bucket is replaced every 7 days. At the same time, considering that temperature changes within a day may affect microbial activities, this system is connected to an instant water heater (China, Guangdong; Honicom RJ2-8.5 kw), so that the system water temperature is stable at 25° C. with the error fluctuating at ±0.1° C.

TABLE 1

Water Quality Test Results during the Experiment

| test index | SBWL | CASS | test index | SBWL | CASS |
|---|---|---|---|---|---|
| $Fe^{3+}$ (mg/L) | 0.02-0.98 | 0.02-0.28 | $Mn^{2+}$ (mg/L) | 0.028-0.019 | <0.001 |
| $Ca^{2+}$ (mg/L) | 45.8-67.5 | 12.1-18.3 | pH | 7.8-8.3 | 9.4-9.8 |
| $Mg^+$ (mg/L) | 15.9-26.0 | 8.87-15.2 | $Cl^-$ (mg/L) | 106.2-125.4 | 50.3-66.8 |
| TP (mg/L) | 1.59-4.02 | 3.77-4.15 | $SO_4^{2-}$ (mg/L) | 91.1-109.5 | 90-114.7 |
| TN (mg/L) | 19.8-26.5 | 20.7-24.7 | total hardness | 280.3-320.9 | 73.1-92.4 |
| $COD_{cr}$ (mg/L) | 54.5-60.8 | 51.2-61.8 | Alkalinity | 251-365 | 168-226 |
| $BOD_5$ (mg/L) | 15.9-26.3 | 12.8-20.9 | Total number of bacteria (cfu · $mL^{-1}$) | $9.3 \times 10^4$ | $8.2 \times 10^4$ |

Note:
TP for total phosphorus; TN for total nitrogen

TABLE 2

Characteristic Parameters of Irrigation Emitter Flow Channels for Biofilm Cultivation

| No | Flow of the irrigation emitter q (L/h) | Flow regime coefficient x | Flow coefficient $K_4$ | Geometric parameters of follow channel (length & width & depth/mm) | Irrigation emitter structure | Produces |
|---|---|---|---|---|---|---|
| $E_1$ | 1.05 | 0.510 | 3.16 | 32.16 × 0.68 × 0.67 | N serrated and angular shape | Netafim Israel |
| $E_2$ | 1.00 | 0.506 | 3.20 | 35.00 × 0.50 × 0.52 | Serrated arc shape | Beijing China |
| $E_3$ | 1.20 | 0.503 | 3.64 | 35.79 × 0.63 × 0.52 | Serrated arc shape | Beijing China |
| $E_4$ | 1.60 | 0.500 | 4.35 | 35.79 × 0.53 × 0.75 | V serrated and angular | Netafim Israel |
| $E_5$ | 1.90 | 0.507 | 5.13 | 26.98 × 0.63 × 0.52 | Serrated arc shape | Beijing China |
| $E_6$ | 2.80 | 0.504 | 8.27 | 41.13 × 0.67 × 0.95 | Serrated arc shape | Beijing China |

(2) Extraction of Key Bacteria in Biofilm

When the biofilm cultivating systems run for 784 hours and the clogging degrees of the irrigation emitters reach 50%, the biofilms shall be extracted from reclaimed water emitters with two treatment processes.

Use a sterilized knife to carefully peel off the irrigation emitters and place them in a 50 ml centrifuge tube, add an appropriate amount of deionized water, and then place them in an ultrasonic cleaner with a power of 600 kW to oscillate and clean for 5 minutes. Repeat the operation for 8-10 times, and control the water temperature as 4° C., collect water sample as biofilm sample.

Centrifuge the water sample at 14000 r/min for 15 min (4° C.), and collect the precipitate for DNA extraction. The total DNA shall be extracted according to the E.Z.N.A.® soil kit (Omega Bio-tek, Norcross, GA, U.S.) instructions. The DNA concentration and purity are tested by NanoDrop2000; and the DNA extraction quality is tested by 1 agarose gel electrophoresis. The V3-V4 variable region of 16S rRNA is PCR amplified by 338F (5'ACTCCTACGG-GAGGCAGCAG-3'-SEQ ID No.: 1) and 806R (5'-GGAC-TACHVGGGTWTCTAAT-3'-SEQ ID No.: 2) primers. The amplification procedure is: 95° C. pre-denaturation 3 min, 27 Cycles (denaturation at 95° C. for 30 s, annealing at 55° C. for 30 s, extension at 72° C. for 30 s), and finally extension at 72° C. for 10 minutes (PCR instrument: ABI GeneAmp® 9700). The amplification system is 20 ul, 4 ul 5*FastPfu buffer solution, 2 ul 2.5 mM dNTPs, 0.8 ul primer (5 uM), 0.4 ul FastPfu polymerase; 10 ng DNA template.

The 338F primer and 806R primer artificial DNA sequences are provided in the ASCII text file, entitled "Sequence Listing_338F_806R", created on Jun. 15, 2022, and having a file size of 1 kilobyte which is hereby incorporated by reference in its entirety.

After the amplification, the PCR product is recovered using 2% agarose gel, and then purified by AxyPrep DNA Gel Extraction Kit (Axygen Biosciences, Union City, CA, USA), eluted by Tris-HCl, and detected by 2% agarose gel electrophoresis. QuantiFluor™-ST (Promega, USA) is used for detection and quantification. Use 2% agarose gel electrophoresis to check the amplification effect.

Figure 2:
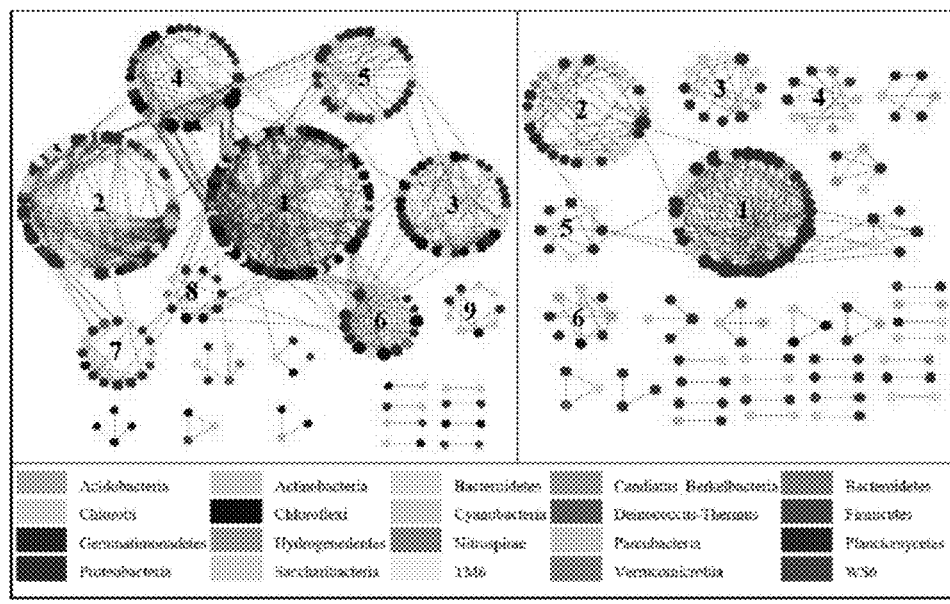
FIG. 2 is an analysis diagram of the bacterial community network in the epiphytic biofilm in the pipeline.

The PCR-amplified and purified product (each processing contains 7 replicates) is sent to Shanghai Majorbio Technology Co., Ltd. for high-throughput biomembrane sequencing analysis. Using the DNA sequencing result to construct the phylogenetic molecular ecological network; and analyze the network. Constructing by the interface method of molecular ecology based on the random matrix theory, using MENA for network analysis, and the visualized network diagram is implemented using Cytoscape 3.3.0, as shown in FIG. 2.

The specific steps are as follows:

First, according to the sequencing result, the original data of OTU abundance matrix is obtained. Each row corresponds to an OTU (operational taxonomic unit, here a strain), and each column corresponding to the abundance of OTU in different samples. The original data is processed by lg standardization.

The MENA analysis website is used to calculate the Pearson correlation of any two OTU and then the correlation matrix is constructed; the correlation matrix is converted into a similarity matrix; one similarity threshold is automatically set according to the principle of random matrix; and then convert the similarity matrix into an adjacency matrix to calculate the connection strength between OTU nodes.

Based on the default threshold, use the MENA network analysis (analyze the networks) to calculate the network property parameters. Use Cytoscape 3.4.0 software to visualize the network; get the network structure diagram and related information: the number of nodes, that is, the strains in the community (OTU); the connection between nodes, that is, the interaction relationship between species (positive correlation, co-occurrence; negative correlation, competition); connectivity, the connection strength between a node and its other connecting nodes; geodesic distance, the shortest distance between two nodes; clustering coefficient, the connectedness between a node and other nodes; modularity, the module feature in a molecular ecological network. A network is divided into multiple modules. And a single module is considered as a functional unit in the ecosystem.

Finally, use the Maslov-Sneppen method, without changing the number of original network nodes and connections, to reconnect nodes at different locations in the original network and construct 100 random networks; and then compare the molecular ecological network and the random networks to find their differences, so as to verify the non-randomness of the constructed molecular ecological network.

After the molecular ecological network analysis is completed, identify key bacteria by the following principle: the molecular ecological network of the biofilm bacterial community can reflect the interaction between the colonies. Among them, those whose OTU have a large number of links with other OTU are the key bacteria that affect the growth of biofilm. Controlling the key bacteria can inhibit the growth of biofilm, so as to remove the biofilm in drip irrigation emitter.

A total of 350 modes and a total of 179 nodes have been obtained for the two process methods, with the number of connections as 1286 and 331 respectively. For the two process methods of CASS and SBWL, the bacteria with most links in the colony are OTU_346: Leptolyngbya and OTU_585: Bosea, respectively, either of which is the key bacteria in the microbial interaction network of the biofilm in corresponding process system.

(3) Screening of Antagonistic Bacteria

Figure 3:
FIG. 3 shows the results of the bacterial antagonist antagonism test.
Figure 4:
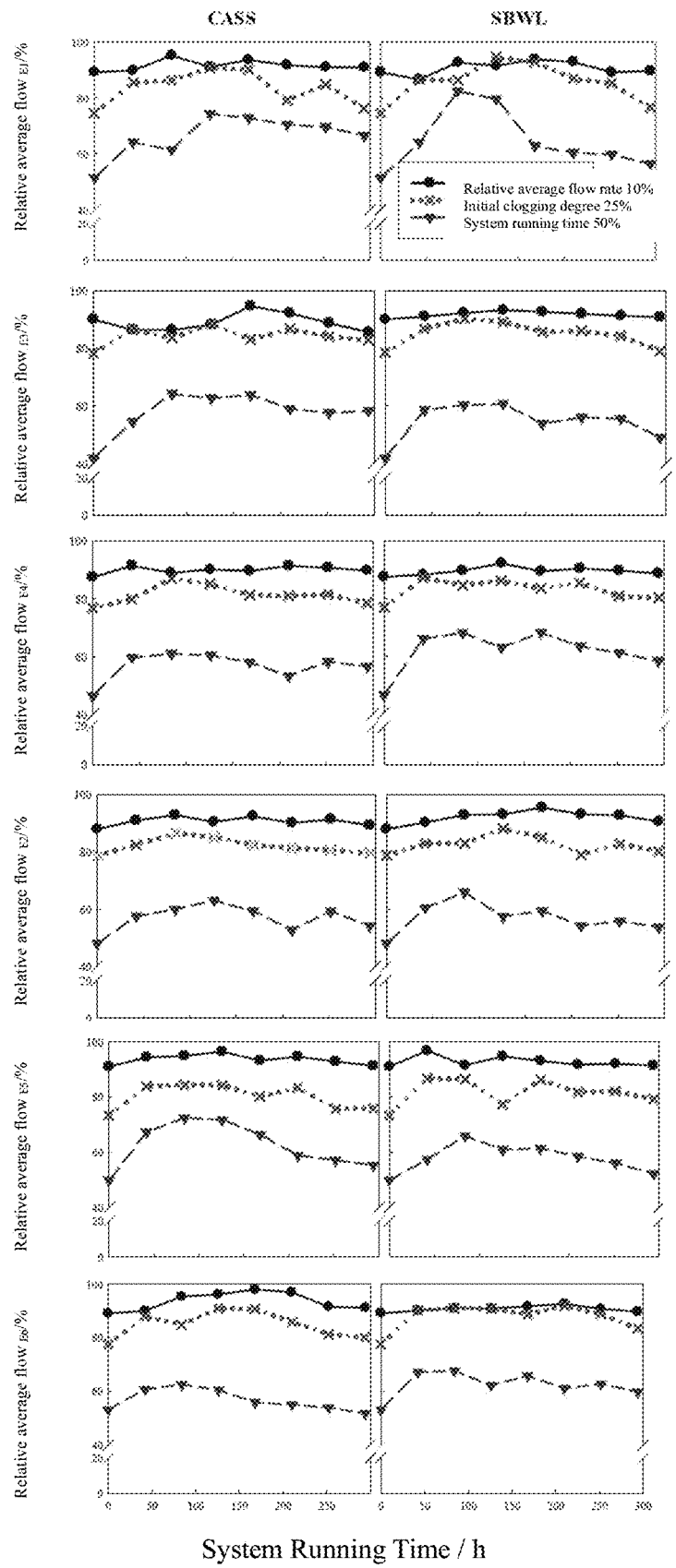
FIG. 4 shows the relative average flow rate change over 300 hours of the irrigation emitter when used in reclaimed water sources processed by cyclic activated sludge system (CASS) versus sequencing batch aeration wastewater recycling technology (SBWL).

For the strains with biological control and rhizosphere growth-promoting functions, *Pseudomonas*, endophytic *bacillus, Bacillus subtilis* and *Bacillus amyloliquefaciens* with biological control and rhizosphere growth-promoting functions are selected as candidate bacteria to implement biofilm antagonism test. The key bacteria obtained in the previous step and the candidate bacteria selected are extracted and purified, and cultivated on a new plate medium for 24 hours. Then on the plate, with the middle biofilm strain as the center, smear microbial inoculum and bacterial strain on the edge of the plate. Only on the plates of *Bacillus subtilis* and *Bacillus amyloliquefaciens*, both candidate bacteria and key bacteria have poor growth. So *Bacillus subtilis* and *Bacillus amyloliquefaciens* are antagonistic bacteria strains (see FIG. 3).

(4) Preparation of Bacterial Antagonist

The nutrient content of biogas slurry is high, and with high output. It is a good organic fertilizer source for drip irrigation. By fermenting the extracted antagonistic bacteria in a basic medium with biogas slurry as the main body, the dominant antagonistic bacteria that can survive and control in biogas slurry environment.

The steps are as follows:

(1) Select the fresh aerogenic biogas slurry from the biogas digester and put it into a reactor in vacuum state for concentration; the concentrating pressure is 1×105 Pa. The slurry is concentrated to moisture content as about 60%; and the concentrating time is about 1 h.

(2) Add the selected antagonistic bacteria, sodium selenite and brown sugar to the biogas slurry to promote the conversion of inorganic selenium (sodium selenite) into organic selenium, so as to generate a liquid bacterial fertilizer rich in organic selenium.

(3) The mixed slurry is uniformly stirred and fermented for 7 days at a temperature of 25-28° C. to obtain a stable multifunctional liquid biogas fertilizer containing antagonistic bacteria stains.

(4) Apply micro-nano bubbles to the multifunctional liquid bacterial fertilizer for half an hour. The aeration process is conducive to the oxidation and decomposition of organic matter in the biogas slurry, so as to reduce the biological toxicity of the biogas slurry and improve the available nutrient.

(5) In view of step (4) micro-nano bubble aeration, the antagonistic bacteria should be screened and selected to be antagonistic bacteria strains that can have a dominant position under strong oxidation condition to ensure the effectiveness of the antagonist. At the same time, the contact of dissolved oxygen with microorganism and organic matter is used to eliminate the inferior anaerobic bacteria in the antagonistic bacteria stain cultivation.

By this method, we can produce a selenium-rich liquid bacterial antagonist with clogging control, biological control and rhizosphere growth promoting effects.

The specific steps in this implementation are as follows: select the fresh aerogenic biogas slurry and put it into a reactor in vacuum state for concentration; the concentrating pressure is 1×105 Pa; The slurry is concentrated to moisture content as about 60%; and the concentrating time is about 1 h; Then according to parts by weight, mix 85 parts of biogas slurry, 8 parts of *Bacillus subtilis* or *Bacillus amyloliquefaciens*, 0.3 parts of sodium selenite and 6.7 parts of brown sugar together; stir and ferment for 7 days at 25° C., and then apply micro-nano bubbles for 0.5 h. A bacterial antagonist containing *Bacillus subtilis* or *Bacillus amyloliquefaciens* is obtained.

(5) Application of Bacterial Antagonist

The unconventional water drip irrigation system has a working pressure of 1.0 MPa. Considering the system requirements and soil conditions, a drip irrigation tape with a flow rate of about 1.0 to 3.0 L/h is selected as the drip irrigation emitter when the relative average flow of the irrigation emitter drops by 25% or after the system has been running for 100 hours, the produced antagonist is mixed in the drip irrigation source water in a ratio of 1:1000, and then input into the drip irrigation system. Normally, it is applied periodically as 1 time/1-2 weeks, with each application time as 2-3 hours, so to avoid the formation of new dominant bacteria in the drip irrigation system which may increase the clogging after the antagonist removes the biofilm. In this mode, the clogging material in the irrigation emitter can be effectively controlled to ensure the safe operation of the system.

(6) Application of Multifunctional Liquid Bacterial Fertilizer

The biofilm control experiment is carried out on emitter samples of reclaimed water drip irrigation system with the relative average flow decreased by 10%, 25%, and 50% in the first stage of epiphytic biofilm cultivation. The bacteria solution and source water are mixed at a ratio of 1:1000 and then added to the drip irrigation system for running. The system shall run a total of 300 h. Apply once every 50 h, and each application of 2 h. Through the regular flow test results, it is found that the application of bacterial antagonist can achieve a clogging control effect on the emitters whose relative average flows decrease by 10% and 25% (see FIG. 4). In view of the need for a bacterial antagonist in the practical drip irrigation on crops, the bacterial antagonist can be applied when the relative average flow of the drip irrigation emitter decreases by 25%.

The invention claimed is:

1. A method for inhibiting microbial clogging of a drip irrigation emitter when the clogging degree of the drip irrigation emitter reaches at least 50%, comprising the following steps:

i) determining a key bacteria causing the clogging of the drip irrigation emitter using developmental molecular ecological network analysis (MENA), via a MENA network analysis system capable of calculating a correlation among an array of bacteria, to construct and analyze a phylogenetic molecular ecological network;

ii) performing screening of an antagonistic bacteria to inhibit the clogging of the drip irrigation emitter;
wherein the steps of using developmental molecular ecological network analysis to determine the key bacteria causing the clogging of the drip irrigation emitter and the screening of an antagonistic bacteria comprise:
  a. cultivating an epiphytic biofilm located in a channel of the drip irrigation emitter,
  b. extracting a sample of microorganisms in the epiphytic biofilm,
  c. extracting the total DNA of the sample of microorganisms in the epiphytic biofilm,
  d. expanding and purifying the V3-V4 variable region of 16S rRNA originating from the total extracted DNA of step ii) c.,
  e. quantitatively detecting and sequencing the V3-V4 variable region of 16S rRNA to obtain an RNA sequence listing,
  f. applying the sequencing result of the sample of microorganisms to construct a phylogenetic molecular ecological network,
  g. determining the key bacteria causing the clogging based on the correlation among the array of bacteria; at the same time, according to the crops to be irrigated, selecting a candidate bacteria having biological control function from the array of bacteria, and
  h. combining the key bacteria and the candidate bacteria to conduct an antagonism experiment; wherein the strains in the candidate bacteria having an antagonistic effect against the key bacteria are used as a selected antagonistic bacteria;
iii) fermenting the selected antagonistic bacteria in a medium containing a fresh biogas slurry, wherein the steps to generate the selected antagonistic bacteria include:
  a. concentrating the fresh biogas slurry by spacing the fresh biogas slurry into a reactor in a vacuum state for concentration using a concentrating pressure of $1 \times 10^5$ Pa, wherein the fresh biogas slurry is concentrated to a moisture content of about 60%, and
  b. fermenting and cultivating the fresh biogas slurry and a pathogenic microorganism to generate the selected antagonistic bacteria; and
iv) applying the selected antagonistic bacteria to a drip irrigation system, wherein the application is a periodic application with a frequency of 1 time every 1 to 2 weeks, and 2 to 3 hours of each application.

2. The method according to claim 1 wherein the construction and analysis method of the phylogenetic molecular ecological network is as follows:
  i) performing a standardizing treatment on an abundance matrix of OTU (operational taxonomic unit) of each strain;
  ii) using the MENA network analysis system to calculate the connection strength between OTU nodes; and
  iii) performing visual processing to obtain a network structure diagram; and determine the OTU with a high number of links with other OTUs, wherein the OTU with a high number of links with other OTUs comprises the key bacteria affecting the growth of the epiphytic biofilm.

3. The method according to claim 1 wherein the bacterial species with biological control function includes: a pathogenic microorganism that may cause crop disease during the growth period of drip irrigation crops and a probiotic bacteria in the roots of crops that promote crop growth.

4. The method according to claim 3 wherein the pathogenic microorganism includes bacteria, viruses, fungi or other pathogenic bacteria; and the probiotic bacteria includes *Agrobacterium, Azotobacter, Azospirillum, Bacillus, Burkholderia, Pseudomonas, Micrococcus, Rhizobium*, or *Frankia*.

5. The method according to claim 1 wherein the concentrating method includes the concentrating time of about 1 hour.

6. The method according to claim 1 wherein the fermenting and cultivating of the fresh biogas slurry and the antagonistic bacteria includes: in parts by weight, adding 15-20 parts of the antagonistic bacteria, 0.4-0.8 parts of sodium selenite and 6-8 parts of brown sugar into 75-85 parts of the fresh biogas slurry; uniformly stir and ferment this mixed biogas slurry for 4-10 days at a temperature of 25-28° C. to obtain a liquid bacterial fertilizer, and then apply at least one micro-nano bubbles to the liquid bacterial fertilizer to obtain the antagonistic bacteria.

7. The method according to claim 1 wherein the applying of the selected antagonistic bacteria to the drip irrigation system includes: when the relative average flow of the drip irrigation emitter drops by at least 25% or after the drip irrigation system has been running for at least 100 hours, the selected antagonistic bacteria is mixed in the drip irrigation source water in a mass ratio of 1:500-1500, and then input into the drip irrigation system.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: synthesized

<400> SEQUENCE: 1
actcctacgg gaggcagcag 20

<210> SEQ ID NO 2
<211> LENGTH: 20
<212> TYPE: DNA
<213> ORGANISM: Artificial
<220> FEATURE:
<223> OTHER INFORMATION: synthesized

<400> SEQUENCE: 2
ggactachvg ggtwtctaat 20